(12) United States Patent
Forsell (10) Patent No.: US 11,737,756 B2
(45) Date of Patent: *Aug. 29, 2023

(54) IMPLANTABLE TISSUE CONNECTOR (71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 198 days.

This patent is subject to a terminal disclaimer.

(21) Appl. No.: 17/073,475

(22) Filed: Oct. 19, 2020

(65) Prior Publication Data
US 2021/0030417 A1 Feb. 4, 2021

Related U.S. Application Data

(63) Continuation of application No. 15/336,958, filed on Oct. 28, 2016, now Pat. No. 10,806,456, which is a
(Continued)

(51) Int. Cl.
*A61B 17/11* (2006.01)
*A61B 17/00* (2006.01)
*A61F 2/06* (2013.01)
*A61B 1/313* (2006.01)
*A61B 17/32* (2006.01)
*A61B 17/34* (2006.01)
*A61M 5/142* (2006.01)
(Continued)

(52) U.S. Cl.
CPC .......... *A61B 17/11* (2013.01); *A61B 1/3132* (2013.01); *A61B 17/00* (2013.01); *A61B 17/1114* (2013.01); *A61B 17/320016* (2013.01); *A61B 17/3478* (2013.01); *A61F 2/064* (2013.01); *A61M 5/142* (2013.01); *A61M 13/003* (2013.01); *A61M 27/002* (2013.01); *A61B 2017/1107* (2013.01); *A61B 2017/1132* (2013.01); *A61F 2/0077* (2013.01); *A61F 2002/045* (2013.01)

(58) Field of Classification Search
CPC .............. A61B 1/3132; A61B 17/1114; A61B 2017/1107; A61B 2017/1132; A61F 2/007; A61F 2002/045
See application file for complete search history.

(56) References Cited

U.S. PATENT DOCUMENTS

4,086,665 A * 5/1978 Poirier ................. A61M 60/117
138/121
4,368,736 A * 1/1983 Kaster ..................... A61F 2/064
606/153
(Continued)

*Primary Examiner* — Alexander J Orkin (57) ABSTRACT

An implantable tissue connector comprises a conduit and at least one bulge extending outwardly from the conduit's outer surface in a circumferential direction. At least one blocking ring loosely fitting over the outer surface with a clearance between the outer surface and the blocking ring is provided for mounting tubular living tissue within the clearance. The blocking ring has an inner diameter which is sized relative to an outer diameter of the bulge to prevent the blocking ring from slipping over the bulge when living tissue is mounted within the clearance. During implantation, the conduit is inserted into the tubular part of living tissue and over the bulge. Then, the blocking ring is pushed over the free end of the living tissue against the bulge. The living tissue is secured to the conduit with a self-enhancing effect when the tissue tends to be pulled off of the conduit.

15 Claims, 4 Drawing Sheets

Related U.S. Application Data continuation of application No. 12/682,533, filed as application No. PCT/EP2008/008590 on Oct. 10, 2008, now Pat. No. 9,480,551.

(60) Provisional application No. 60/960,790, filed on Oct. 15, 2007, provisional application No. 60/960,767, filed on Oct. 12, 2007, provisional application No. 60/960,765, filed on Oct. 12, 2007, provisional application No. 60/960,764, filed on Oct. 12, 2007, provisional application No. 60/960,766, filed on Oct. 12, 2007, provisional application No. 60/960,715, filed on Oct. 11, 2007, provisional application No. 60/960,716, filed on Oct. 11, 2007.

(51) Int. Cl.
*A61M 13/00* (2006.01)
*A61M 27/00* (2006.01)
*A61F 2/00* (2006.01)
*A61F 2/04* (2013.01)

(56) References Cited

U.S. PATENT DOCUMENTS

| | | | | |
|---|---|---|---|---|
| 5,769,862 | A * | 6/1998 | Kammerer | A61B 17/0469 606/139 |
| 10,806,456 | B2 * | 10/2020 | Forsell | A61F 2/064 |
| 2004/0153104 | A1 * | 8/2004 | Buckman | A61B 17/11 606/151 |
| 2005/0033226 | A1 * | 2/2005 | Kim | A61F 2/04 604/101.01 |
| 2005/0070933 | A1 * | 3/2005 | Leiboff | A61M 3/0283 606/153 |

* cited by examiner

IMPLANTABLE TISSUE CONNECTOR

This application is a continuation of U.S. application Ser. No. 15/336,958, filed Oct. 28, 2016, which is a continuation of U.S. application Ser. No. 12/682,533 filed Apr. 9, 2010, now issued as U.S. Pat. No. 9,480,551, which is the U.S. national phase of International Application No. PCT/EP2008/008590 filed 10 Oct. 2008, which designated the U.S. and claims the benefit of U.S. Provisional Appln. No. 60/960,715 filed 11 Oct. 2007; U.S. Provisional Appln. No. 60/960,716 filed 11 Oct. 2007; U.S. Provisional Appln. No. 60/960,766 filed 12 Oct. 2007; U.S. Provisional Appln. No. 60/960,764 filed 12 Oct. 2007; U.S. Provisional Appln. No. 60/960,765 filed 12 Oct. 2007; U.S. Provisional Appln. No. 60/960,767 filed 12 Oct. 2007; and U.S. Provisional Appln. No. 60/960,790 filed 15 Oct. 2007, the entire contents of each of which are hereby incorporated by reference.

BACKGROUND OF THE INVENTION

The present invention relates to an implantable tissue connector that is specifically adapted to be connected to a tubular part of living tissue within a patient's body, such as to the end of the human's large bowel when an artificial exit to the large bowel is to be provided. However, the implantable tissue connector of the present invention is not limited to such application and can be used in connection with many other kinds of tubular living tissue, as will be described in more detail below.

Connecting the end of the human's large bowel to an artificial exit, such as to a fecal excrements collecting container, or connecting a shortened large bowel to the patient's natural intestinal exit has always proven difficult and often unreliable. Leakage can occur where the connection is not tight over the lifetime. Blood circulation can be prohibited in the end area of the bowel tissue, which can negatively affect the muscle functions and peristaltic movement of the bowel and which can even lead to starvation of the respective portion of the bowel. Furthermore, the peristaltic movement of the bowel will continuously act upon the connection and, thus, the connection can fail over time.

SUMMARY OF THE INVENTION

It is therefore an object of the present invention to provide an implantable tissue connector for connecting tubular living tissue in a patient's body, which connection should be reliable over time and not severely harm the living tissue.

It is a further object to propose different uses for such tissue connector as well as methods for implanting the tissue connector in a patient's body.

Accordingly, the implantable tissue connector of the present invention comprises a conduit with at least a first and a second end and further having an outer surface.

According to the invention, there are provided special elements for preventing the tubular tissue from slipping off of the conduit. More particularly, the tissue connector comprises at least one bulge extending outwardly from the conduit's outer surface in a circumferential direction of the conduit about at least part of the conduit's circumference. Furthermore, at least one blocking ring is loosely fitted over the outer surface of the conduit with a clearance between the conduit's outer surface and the blocking ring for mounting living tissue within said clearance. The blocking ring has an inner cross sectional diameter which is smaller than or substantially identical to an outer cross sectional diameter of the at least one bulge so as to prevent the blocking ring from slipping over the bulge when living tissue is mounted within the clearance.

When the tissue connector is implanted in a human being or animal, the living tissue will be pulled over the conduit's outer surface including the bulge. Then the blocking ring will be advanced from the other side of the bulge over the living tissue towards the bulge such that at least part of the living tissue is located intermediate the conduit's outer surface and the blocking ring. This has the effect that, when the tissue tends to slip off of the conduit, it will carry the blocking ring towards and against the bulge. By this action, the living tissue will be compressed between the bulge and the blocking ring, thereby preventing any further slippage. This effect is self-enhancing with increasing slipping force. As the force tends to decrease again, the compression force will decrease accordingly so that blood circulation within the living tissue will not be negatively affected longer than necessary. Thus, the connection will be reliable over time and not severely harm the living tissue.

The size of the clearance in a radial direction depends upon the intended use of the tissue connector, i.e. upon the thickness of the tubular living tissue to which the tissue connector is connected. Accordingly, the size may be at average between 0.1 to 0.4 mm, 0.4 to 0.8 mm, 0.8 to 1.3 mm, 1.3 to 2 mm, 2 to 3 mm, 3 to 4 mm, 4 to 5 mm, over 5 mm. The clearance should be slightly smaller than the thickness of the living tissue so as not to severely affect blood circulation within the living tissue but nevertheless ensure sufficient frictional contact.

While the cross-sectional diameter of the blocking ring should preferably be smaller than the cross-sectional diameter of the bulge, it can in some instances be identical or even somewhat larger than this because the thickness of the living tissue, even in a compressed state, adds up to the cross-sectional diameter of the bulge so that altogether the blocking ring is prevented from slipping over the bulge. Therefore, in case of particularly thick living tissue, the inner cross-sectional diameter of the blocking ring may be even somewhat larger than the outer cross-sectional diameter of the bulge.

In the regards of materials, both the conduit and the blocking ring should preferably be made from biocompatible material. This preferably comprises polymers, such as polytetrafluoroethylene (PTFE), ePTFE, silicone, polyurethane and/or polyetheretherketone (PEEK). However, other materials, such as ceramics and metals, in particular titanium and stainless steel, can be used as well and are preferable for their strength.

The conduit can be substantially longer than the particular portion of the conduit to which the tubular tissue is connected. In that case, it is preferable that the bulge is located proximately to the respective end of the conduit so that the part of the tissue drawn over the conduit is not excessively large. The larger the overlapping part of the tissue is, the larger may become problems of blood circulation within that part of the tissue.

Where the tissue connector is intended to connect two different ends of tubular living tissue material, it may have two of the aforementioned bulges, preferably located proximately to the respective ends of the conduit, with at least one and preferably at least two blocking rings located intermediate the two bulges. Of course, more than one blocking ring and/or more than one bulge may be provided for each end of the conduit.

In order to facilitate the step of inserting the end or ends of the conduit into the tubular living tissue, it is advantageous to taper the free end portion of the conduit's end or ends towards the edge of said free end portion. Alternatively or in addition, the free end portion may be provided with a rounded edge. The rounded edge will help to prevent any damage to the living tissue when the tissue is pulled over the free end of the conduit.

As mentioned at the outset, the use of the tissue connector of the present invention is not limited to its application at the end of the human's large bowel. It can be advantageously used in many other applications.

For instance, the tissue connector may be fitted into a human's esophagus. In this case, the conduit of the tissue connector should have an inner diameter of between 2 and 3.5 cm to provide for a snug fit. The clearance between the conduit and the blocking ring should be in the range of 2.5 to 5 mm.

Where the tissue connector is connected to a human's trachea, the inner diameter should be chosen between 1.5 and 2.5 cm, depending upon the position where at the human's trachea it is to be connected, in order to provide for a snug fit. The clearance between the conduit and the blocking ring should be in the range of 1 to 2 mm.

Where the tissue connector is fitted into a human stomach, the inner diameter of the conduit can vary with enlarged boundaries. The clearance between the conduit and the blocking ring should be in the range of 3.5 to 5 mm.

The tissue connector may also be fitted into a human's gall bladder or its connecting outlet channels. In that case, the conduit should have an inner diameter of between 0.5 and 1.3 cm. The clearance between the conduit and the blocking ring should be in the range of 0.5 to 1.5 mm.

In case that the tissue connector is fitted into a human's small bowel, the inner diameter of the conduit should be between 2 and 3 cm. The clearance between the conduit and the blocking ring should be in the range of 3 to 4 mm.

In case of the human's large bowel, whose diameter is highly stretchable, the inner diameter of the conduit should be between 3 and 5.5 cm to provide for a snug fit. The clearance between the conduit and the blocking ring should be in the range of 2 to 3.5 mm.

The tissue connector may also be fitted into a human's urethra. In this case, the conduit should have an inner diameter of between 0.4 and 0.8 cm. The clearance between the conduit and the blocking ring should be in the range of 0.5 to 1.5 mm.

Also, the tissue connector may be fitted into an human's ureter, in which case the inner diameter of the conduit should be chosen between 0.4 and 0.7 cm. The clearance between the conduit and the blocking ring should be in the range of 2 to 4 mm.

The tissue connector may also be connected to the kidney. In order to snuggly fit it into a human's pelvic part of the kidney, the inner diameter of the conduit should be in the range of 1 and 5 cm, depending upon the position where at the human's pelvic it is to be connected. The clearance between the conduit and the blocking ring should be in the range of 0.5 to 1.5 mm.

The tissue connector may also be fitted into a human's blood vessel. In this case, the inner diameter of the conduit should be chosen approximately similar to the inner diameter of the respective blood vessel. As an example, the inner diameter may be chosen between 0.1 and 0.5 cm in the case of particularly small blood vessels. The tissue connector may as well be connected to the human's aorta or the heart's atrium or ventricle, in which case the inner diameter of the conduit is in the range of 2 to 3 cm. The clearance between the conduit and the blocking ring should be in the range of 1 to 2 mm.

The tissue connector may also be used as an intermediate piece to replace a part of tubular living tissue and may as well be used to connect different types of tubular living tissue, such as where a biological transplant of a third party's body is to be connected to the organs of a patient.

According to a preferred embodiment of the invention, at least one flexible sleeve may be mounted on the outer surface of the conduit such that it axially extends around at least part of said conduit. According to a first embodiment, the flexible sleeve is initially mounted on said outer surface either folded or rolled upon itself. According to a second embodiment, the flexible sleeve is initially mounted on said outer surface so as to be foldable upon itself. According to a third, more general embodiment, the flexible sleeve is not initially mounted on the conduit but will be mounted thereon only at the time of implantation of the tissue connector in the patient's body.

The first end of the conduit of the tissue connector is connected to a tubular part of living tissue by inserting the first end of the conduit including the bulge into the tubular part of living tissue. Where, according to the first embodiment, the flexible sleeve is mounted on the outer surface of the conduit folded or rolled upon itself, the flexible sleeve is unfolded or unrolled such that at least part of the living tissue extending over the conduit's outer surface is located intermediate the sleeve and the outer surface of the conduit. Where, according to the second embodiment, the flexible sleeve is mounted on the outer surface of the conduit so as to be foldable upon itself, the flexible sleeve is folded upon itself such that at least part of the living tissue is located intermediate the folded sleeve or intermediate the conduit's outer surface and the sleeve. Where, according to the third embodiment, the flexible sleeve is provided separate from the conduit, the sleeve is advanced over the conduit and the respective portion of tubular tissue such that at least part of the living tissue is located intermediate the sleeve and the conduit's outer surface. In either of the aforementioned three embodiments, the flexible sleeve may or may not extend over the bulge.

Either way, the tubular tissue is located somewhere between the conduit and the flexible sleeve and can be held in that position in various manners that will be described in the following and that can be applied individually as well as in combination.

The advantages achieved with the tissue connector according to the aforementioned three preferred embodiments comprise a good sealing of the living tissue between the conduit and the flexible sleeve as well as good protection of the living tissue by the flexible sleeve. This way, the connection can be made reliable over time while also protecting the tissue against harm.

Where the flexible sleeve overlaps with the living tissue that has been drawn over the first end of the conduit, it is desirable that the flexible sleeve will exert radial pressure upon the tissue. In instances where strong and/or repeated movement of the tissue material is to be expected, such as when used as a bowel connector, the radial pressure will assist in holding the components in place until they are otherwise fixed against one another. In any case, it is preferable to design the flexible sleeve such that the radial pressure is minimal so as not to prohibit the blood circulation in the living tissue.

Furthermore, the conduit should be designed such that it is less flexible than the flexible sleeve at least in a radial direction so as to provide support to the sleeve against radial forces, in particular against the sleeve's aforementioned radial pressure. This way, the open internal cross section of the conduit will not be affected by the radial forces caused by the flexible sleeve.

Another particularly preferred way of reliably connecting the living tissue to the tissue connector involves a flexible sleeve that comprises a porous ingrowth layer allowing ingrowth of living tissue. This will not only strengthen any connection between the tissue connector and the tissue but will also serve to further seal the connection against any leakage.

The ingrowth layer should be made from a material that stimulates tissue ingrowth. Preferably, the ingrowth layer has a netlike structure that can be penetrated by ingrowing tissue, thereby creating a durable connection between the living tissue and the flexible sleeve. Of course, the ingrowth layer should be made from a biocompatible material, such as Dacron®.

Another way of reliably fixing the living tissue to the tissue connector consists in suturing the flexible sleeve to the living tissue. Alternatively, the suturing may be performed through the flexible sleeve and an outer wall of the conduit including an interposed portion of the living tissue. Thereby, the tissue is fixed to both the flexible sleeve and the conduit. Leakage through needle penetrations caused by the suturing, if any, will automatically close over time by overgrowing tissue material.

It is also possible to perform the suturing through a portion of the living tissue and the outer wall of the conduit before the flexible sleeve is placed over the living tissue. This eliminates any problems of leakage through the penetration holes caused by the suturing as the sleeve will cover and seal such penetration holes.

Preferably, the thread used for suturing is made from a material that is absorbable by the patient's body. Typically, the thread will be absorbed by the body within about 6 weeks. At that time, however, the tissue ingrowth will be sufficiently advanced to compensate for the loss of strength that was initially provided by the thread.

Instead or in addition to suturing the flexible sleeve to the conduit by means of a preferably absorbable thread, the sleeve may be fixedly connected to the conduit along an axially extending portion of the sleeve in any other appropriate way. For instance, the conduit and the sleeve may be bonded along at least part of said axially extending portion of the sleeve. A primer may be applied on the conduit's outer surface and/or the flexible sleeve to enhance bonding characteristics.

The flexible sleeve may comprise a multi-layer material. This is particularly advantageous where the flexible sleeve comprises the aforementioned porous ingrowth layer. For instance, the porous ingrowth layer might itself not be sufficiently stable to be safely handled and pulled over the tubular tissue and/or the porous ingrowth layer might not be able to exert the radial pressure onto the tissue. In either of these cases, it is advantageous to provide the flexible sleeve with a support layer for supporting the porous ingrowth layer.

The support layer may be made e.g. from polyurethane or from expanded polytetrafluoroethylene (ePTFE). ePTFE is particularly preferred as it can be designed with pores sufficiently large in size so as to allow for the necessary exchange of particles and/or elements between the underlying tissue and the surrounding area of the patient's body. Furthermore, the support layer may give better protection to the tissue than the ingrowth layer.

It is preferable when after implantation the support layer forms an outer layer of the flexible sleeve or, at least, that the ingrowth layer will be located radial inward from the support layer. Thus, where the flexible sleeve is mounted on the outer surface of the conduit so as to be foldable up on itself, the ingrowth layer will be located between portions of the support layer when the sleeve is folded upon itself. Alternatively, where the flexible sleeve is mounted on the outer surface of the conduit folded or rolled upon itself, the ingrowth layer will be located radial inward from the support layer when the sleeve is unfolded or unrolled.

Where the tissue connector is intended for connecting with one another two different ends of tubular living tissue, the conduit may have one flexible sleeve at each of the conduit's first and second ends. Again, the flexible sleeves are preferably located proximately to said first and second ends.

Of course, it is again preferable to make the flexible sleeve from a biocompatible material, in particular polymer materials similar to those mentioned above in relation to the conduit (except that PEEK would not be suitable).

The tissue connector may particularly be used and be adapted for connecting it to at last one of an implantable reservoir, an implantable pump, an implantable motor, an implantable medical device and a biological transplant. The artificial items may even form a part of the tissue connector, either integrally formed therewith or separately connected thereto. The reservoir, pump, motor and/or medical device may also be incorporated in the tissue connector between the first and second ends of the conduit.

The biological transplant may be any transplant, such as a transplanted heart to be connected by means of the tissue connector to the patient's aorta and/or to other blood vessels (pulmonary arteria etc.).

Instead of being artificial, the aforementioned reservoir may consist of a biological transplant, but it may as well be made from tissue material of the patient into whom the reservoir is to be implanted. For instance, the reservoir may be a fecal excrements collecting container, such as a urine bladder or an intestine.

The reservoir may also be a reservoir for medical drugs for the patient's needs and is preferably adapted to be filled with at least one medical drug. Such medical drug reservoir may or may not be connected to a medical device, such as an implantable drug delivery device, which medical device may additionally include a pump for pumping the drug from the reservoir into the patient's body and possibly a motor for the pump.

Any other implantable medical devices may also be connected to the organs of the patient by means of the tissue connector, with or without a pump, motor and/or reservoir. Examples of these are an artificial heart, a penile prothesis, an artificial urine bladder, an artificial urethra, an artificial esophagus, an artificial trachea and the like. Examples of biological transplants include a urine bladder, an intestine, a urethra, a ureter, a kidney, a bowel, a heart, an esophagus, a trachea, a blood vessel and the like.

The tissue connector of the present invention can be implanted in a human being or animal either in open surgery or by subcutaneous surgery. In either case, the skin will have to be cut before free-dissecting an appropriate location within the patient's body adjacent to the tubular living tissue and, after the conduit of the tissue connector has been connected with one or both ends to the tubular tissue, at least the skin will have to be sutured at the end of the surgery.

Where the tissue connector is implanted by subcutaneous surgery, the steps of cutting the skin and free-dissecting the appropriate location within the patient's body comprise the steps of inserting a needle-like tube into the patient's body, such as the patient's thorax or abdomen, filling through said needle gas into the patient's body, i.e. into the thorax cavity or abdomen cavity, cutting a key-hole, inserting at least one, preferably two, laparoscopic trocars through the key-hole towards said location, advancing one or more medical instruments and a camera through the at least one trocar towards said location, i.e. into the thorax or abdomen, and dissecting an area of the tubular part of living tissue with the aid of the dissecting tool.

The tissue connector may be supplied to said location through the at least one trocar or through a separate incision.

The invention will now be described in more detail in context with some preferred embodiments of the invention as shown in the accompanying drawings.

Figure 1:
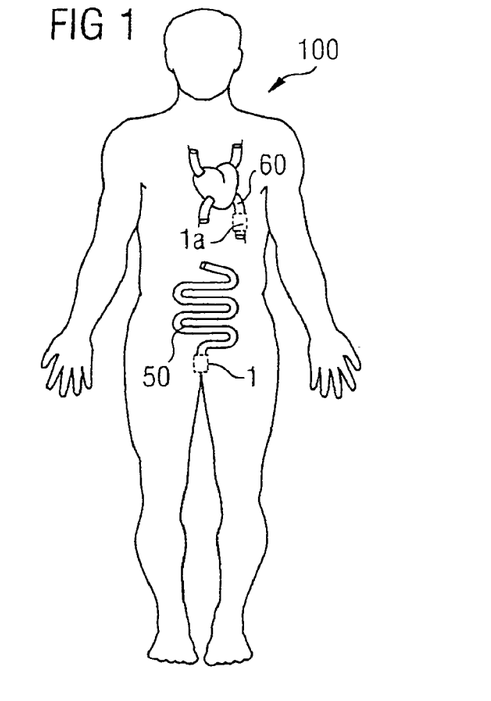
FIG. 1 shows an exemplary view of a patient with one tissue connector connected to the patient's aorta and another tissue connector connected to the end of the patient's large bowel.

FIG. 1 schematically shows a body 100 of a patient with a first tissue connector 1 connected to the end of the patient's large bowel 50 and a second tissue connector 1a interconnecting two pieces of the patient's aorta 60. The tissue connector 1 may either connect the large bowel 50 to the patient's anus or to an artificial anus which may include an excrements collecting container. The tissue connector 1a may include between its two ends a heart valve, a blood pump, a drug delivery device or the like.

The tissue connectors 1 and 1a shown in FIG. 1 represent only a few of many different possible locations and applications of the tissue connector within the human's or, alternatively, an animal's body. Further examples of possible applications have already been outlined further above.

Figure 2:
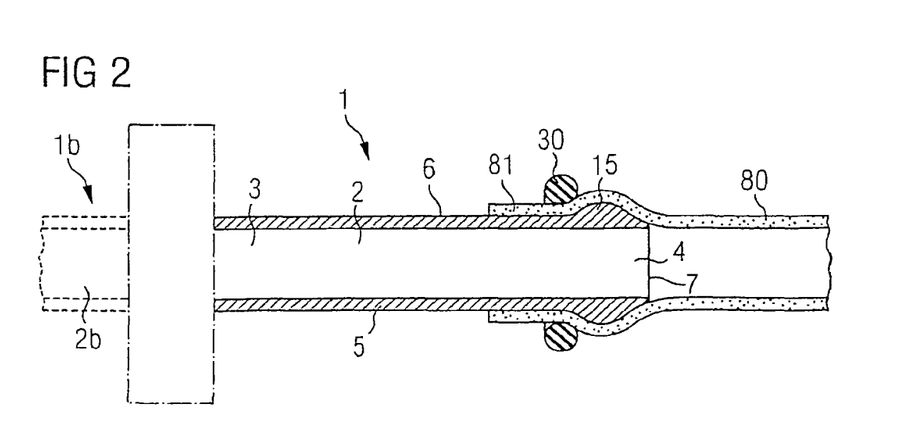
FIG. 2 shows a cross section of a first embodiment of the tissue connector in a state connected to living tissue.

FIG. 2 shows a first embodiment of the tissue connector 1 connected to a tubular part of living tissue 80. The tissue connector 1 comprises a conduit 2 with a first end 3 and a second end 4. The second end 4 of the conduit 2 has already been inserted into an end portion of living tissue 80. The inner cross section of the conduit 2 is selected to approximately match the inner cross section of the tubular living tissue 80 so as not to obstruct any flow of material. The thickness of the wall 5 of the conduit, which is typically circular, is chosen to provide sufficient strength so that it does not collapse under the forces that will act upon the conduit during use, while providing sufficient flexibility where needed. On the other hand, the thickness should not be chosen too large since the living tissue will have to be stretched over the outer surface 6 of the conduit 2 without damage and without excessively affecting blood circulation within the end portion 81 of the living tissue 80.

The wall 5 of conduit 2 is tapered towards its leading edge 7. In addition, the leading edge 7 is rounded. These two measures prevent damage to the living tissue 80 when the conduit 2 is inserted into the end portion 81 of the living tissue 80.

The first end 3 may serve and be adapted to be connected to an implantable medical device, an implantable reservoir, an implantable pump, an implantable motor or a combination of the afore mentioned items (generally designated with 200). It may also be connected to any other implantable device 200. The implantable device 200 may even form a part of the tissue connector 1, either integrally or attached thereto.

The implantable device 200 may also be a medical device replacing one or more of the patient's organs, such as an artificial urine bladder, a fecal excrement's collecting container, an artificial urethra, an artificial heart, an artificial esophagus, an artificial trachea or the like. Alternatively, the first end 3 of the conduit 2 may be connected to a biological implant obtained from a third party's body, such as a urine bladder, an intestine, a urethra, a ureter, a kidney, a bowel, a heart, an esophagus, a trachea, a blood vessel or the like.

The device 200 may also comprise a flow restrictor for partial or complete restriction of flow through the conduit. This can be suitable e.g. in the case where the tissue connector is located at the end of the patient's large bowel.

The device 200 may also be placed between the tissue connector 1 and a second tissue connector 1b with conduit 2b, as is indicated in FIG. 2 by dotted lines. This arrangement is practical where the device 200 has to be placed at a location within one of the patient's organs, such as in a blood vessel, in which case the blood vessel would be divided and the device 200 placed between the two tissue connectors 1 and 1b connected to the respective free ends of the divided blood vessel. As an example, the device 200 could include a flow restrictor, such as an artificial heart valve, or a drug delivery reservoir.

Apart from the conduit 2 and the optional device 200, the tissue connector 1 of the embodiment shown in FIG. 2 has a bulge 15 that extends outwardly from the conduit's outer surface 6 in a circumferential direction of the conduit 2 about at least a part of the conduit's circumference. Furthermore, at least one blocking ring 30 loosely fitting over the outer surface 6 of the conduit 2 with a clearance between the outer surface 6 and the blocking ring 30 is provided for mounting the tubular living tissue 80 within the clearance. The blocking ring has an inner cross-sectional diameter which is about the same as the outer cross-sectional diameter of the bulge 15. This prevents the blocking ring from slipping over the bulge when the living tissue 80, as shown in FIG. 2, is mounted within the clearance.

When an axial force tends to pull the tubular living tissue 80 from the outer surface 6 of the conduit 2, the blocking ring 30 will move with the tubular tissue 80, thereby compressing the tubular tissue 80 against the bulge 15, so as to prevent any further slippage of the tubular tissue 80 over the bulge 15. This is a self-enhancing effect. Preferably, the blocking ring in this and in the subsequently described embodiments is made from a material that has a friction coefficient in relation to living human (outer) mucosa tissue that is higher than a friction coefficient which the conduit's outer surface has in relation to living human (inner) serosa tissue.

Figure 3:
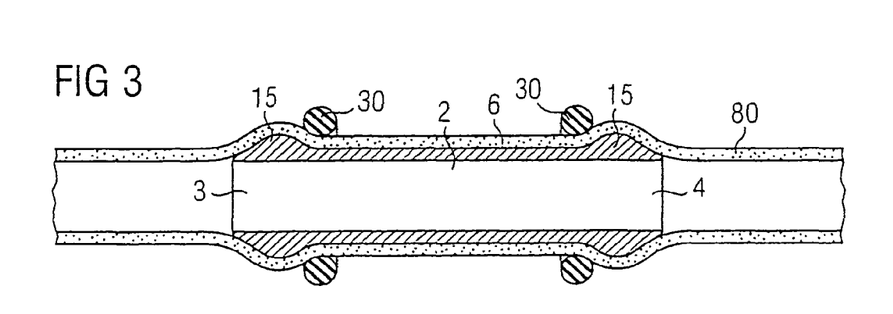
FIG. 3 shows a second embodiment of the tissue connector with two connecting ends.

FIG. 3 shows a second embodiment of the tissue connector 1 comprising the conduit 2 with each of its first and second ends 3 and 4 having a circumferential bulge 15. Between the two bulges 15 two blocking rings 30 are arranged. Tubular living tissue 80 has been pulled over the conduit 2 and through the blocking rings 30, and the blocking rings 30 have then been pushed into a position closest to the bulges 15. Therefore, when stretching forces are applied to the tubular tissue 80 in the one or the other direction, depending upon the direction one of the two blocking rings 30 will move towards the associated bulge 15, thereby clamping the tissue 80 between the blocking ring 30 and the bulge 15 and prohibiting any further slippage of the tissue 80 off the conduit 2.

The embodiment shown in FIG. 3 is particularly suitable to strengthen weak sections in a tubular part of living tissue or to seal a porous section, such as a porous section of the patient's intestine.

The same tissue connector as shown in FIG. 3 may also be used to connect two separate ends of tubular tissue or to connect one end of tubular tissue with another end of a hose or the like that may lead e.g. to an implantable medical device or to an exit port, such as an artificial body exit.

Figure 4:
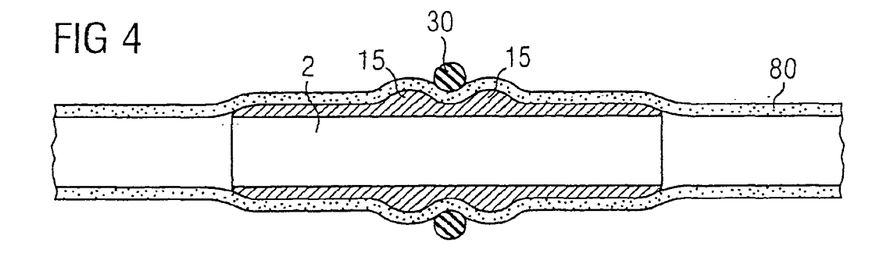
FIG. 4 shows a third embodiment of the tissue connector as an alternative to the second embodiment.

FIG. 4 shows a third embodiment that can be used as an alternative to the embodiment previously discussed in relation to FIG. 3. Again, the conduit 2 has two bulges 15 to prevent the tubular tissue 80 from slipping off of the conduit. However, in this embodiment the bulges 15 are arranged in close proximity to one another so that a single blocking ring 30 located between the two bulges 15 in an axial direction of the conduit will be sufficient to cooperate with one or the other of the two bulges 15 depending upon the direction of the stretching force acting upon the tissue 80.

Figure 5A:
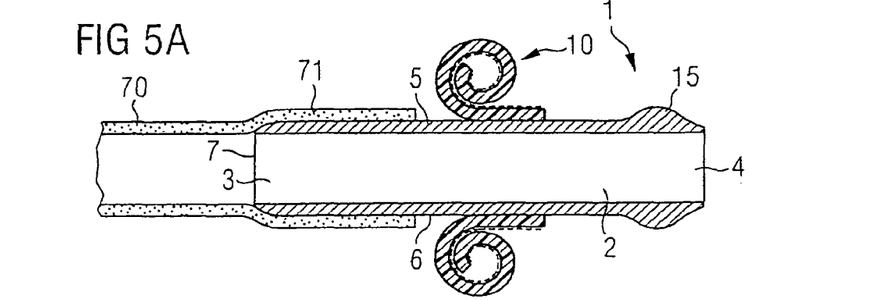
FIGS. 5a and 5b show an alternative for mounting living tissue on a free end of the tissue connector.
Figure 5B:
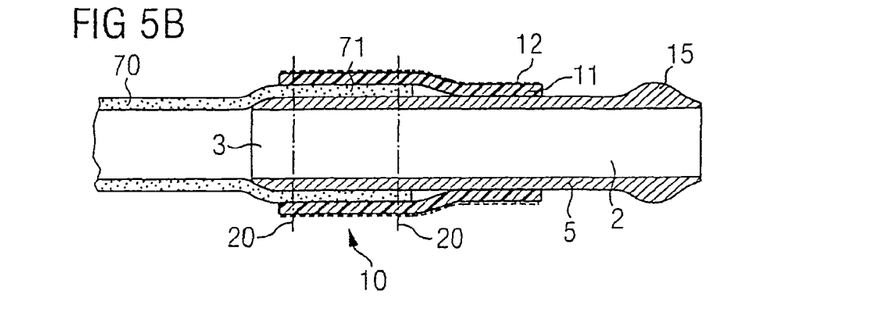

FIGS. 5a and 5b show an alternative for mounting living tissue on the free end 3 of the tissue connector 1 to either another part of living tissue 70 or to a hose. Apart from the conduit 2 and the bulge 15 at the second end of the conduit 2, the tissue connector 1 of the embodiment shown in FIG. 5a has a flexible sleeve 10 axially extending and closely fitted around a part of the outer surface 6 of the conduit 2. The flexible sleeve 10 may be delivered separately from the conduit 2 and placed over the conduit's outer surface 6 shortly before implantation into the patient's body. However, it is preferred to provide the conduit 2 with the flexible sleeve 10 as a unitary item, the flexible sleeve 10 preferably fixed to the outer surface 6 by means of bonding, welding and/or clamping. In the case of bonding, it can be advisable to pretreat the outer surface 6 e.g. with a primer, depending upon the material combination to be bonded together.

In FIG. 5a, the flexible sleeve 10 is rolled upon itself and can be unrolled over the portion 71 of living tissue 70 so as to cover, seal and protect that portion 71 on the first end 3 of the conduit 2, as is shown in FIG. 5b. The tissue portion 71 and the overlapping part 11 of flexible sleeve 10 are fixed to the first end 3 of the conduit 2 by suturing threads 20 therethrough and through the wall 5 of the conduit 2, as is indicated in FIG. 5b by dotted lines.

The flexible sleeve 10 is a multilayer material comprising a porous ingrowth layer to allow ingrowth of living tissue. For that, it has a netlike structure. On top of the ingrowth layer 11 there is provided a support layer 12. The support layer 12 may have one ore more of various functions. One possible function is to provide support to the ingrowth layer 11 so as to ease handling and/or prevent fussing of the ingrowth layer. Also, the support layer 12 may provide some tension, thereby exerting a compressive force in a radial direction so as to slightly clamp the tissue portion 71 against the outer surface 6 of the conduit 2. For that, the support layer should have an appropriate elasticity. Finally, the support layer may provide protection for the tissue portion 71.

Preferably, the support layer should be porous so that exchange between the tissue portion 71 and the surrounding area within the patient's body is possible. This is an important aspect for the ingrowth of living tissue material into the ingrowth layer 11. Expanded polytetrafluoroethylene (ePTFE) is particularly suitable, as it is flexible, inert and can be made with any desired porosity. Other biocompatible polymers, such as polyurethane and the like, are suitable as well.

Figure 6A:
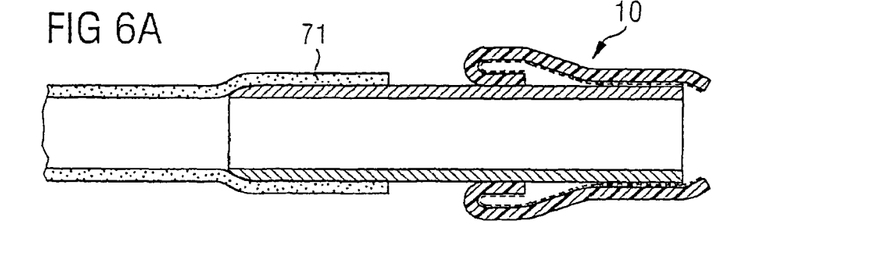
FIGS. 6a and 6b show another alternative for mounting living tissue on a free end of the tissue connector.
Figure 6B:
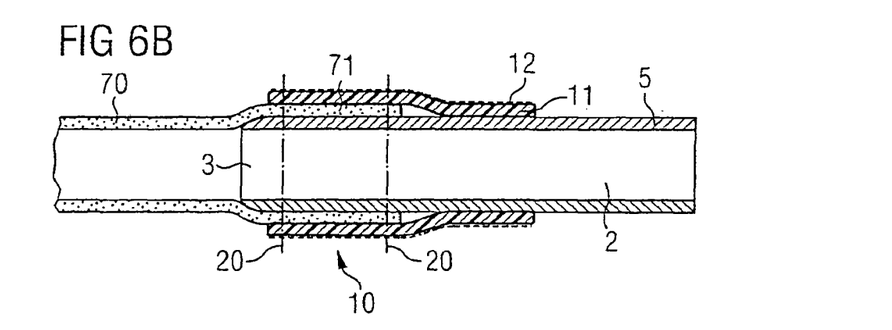

FIGS. 6a and 6b show an alternative which differs from the connector shown in FIGS. 5a and 5b solely by the fact that the flexible sleeve 10 is not rolled upon itself but, instead, folded upon itself. By unfolding the folded sleeve 10, it can be placed over the tissue portion 71 in the same manner as discussed above in relation to FIGS. 5a, 5b, as is shown in FIG. 6b.

Figure 7A:
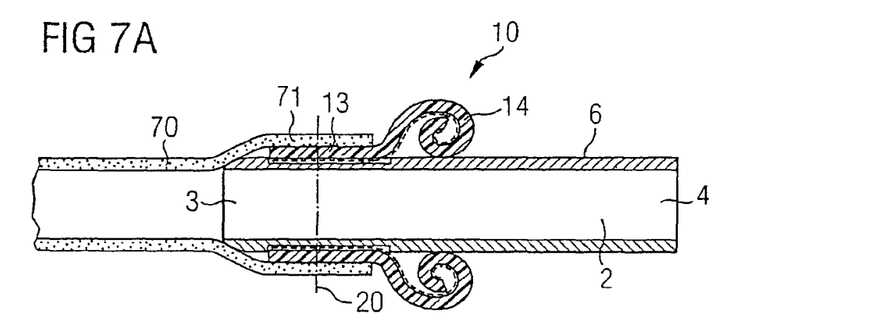
FIGS. 7a and 7b show a further alternative for mounting living tissue on a free end of the tissue connector.
Figure 7B:
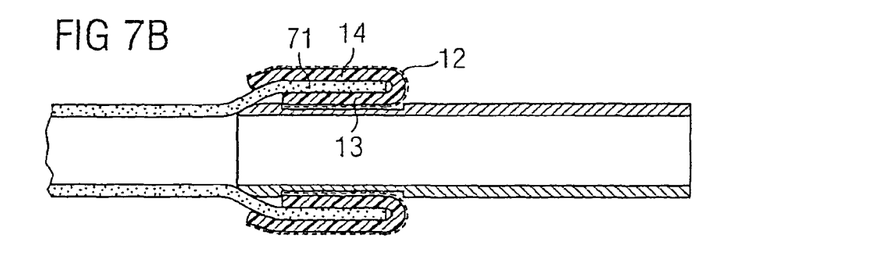

FIGS. 7a and 7b show another alternative where the flexible sleeve 10 is arranged such that it is foldable upon itself. More particularly, the first end 3 of the conduit 2 is inserted in the tissue portion 71 of living tissue 70 to an extent that it overlaps a first portion 13 of the flexible sleeve 10. The remaining portion 14 of the flexible sleeve 10 not being covered by the tissue portion 71 is rolled upon itself and can be unrolled so as to cover the tissue portion 71. As a result shown in FIG. 7b, the flexible sleeve 10 is folded upon itself with the tissue portion 71 placed intermediate the folded sleeve 10.

Different to the alternatives described before, suturing the tissue portion 71 to the wall 5 of the conduit 2 is carried out before the tissue portion 71 is covered with the remaining part 14 of the flexible sleeve 10. The remaining part 14 thereby seals any penetration holes caused by the suturing.

In an even further alternative, not shown, the first end 3 of the conduit 2 will be inserted in the tissue portion 71 only so far that the tissue portion 71 does not overlap with the flexible sleeve 10. Thus, after unrolling the flexible sleeve 10, only a part of the folded sleeve 10 will cover the tissue portion 71.

Furthermore, also not shown, the remaining part 14 of the sleeve 10 is not necessarily rolled upon itself, as shown in FIG. 7a, but may lay flat against the outer surface 6 of the conduit 2, similar to the embodiment shown in FIG. 6a.

As will be recognized, the portion 13 of the flexible sleeve 10 is arranged in a circumferential groove provided in the outer surface 6 of the conduit 2. It is advantageous when the depth of the groove corresponds to the thickness of the flexible sleeve 10. This will facilitate introducing the first end 3 of the conduit 2 into the living tissue 70.

Figure 8A:
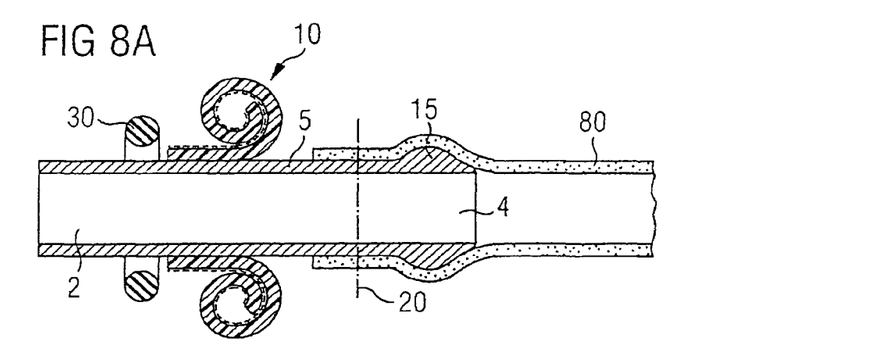
FIGS. 8a and 8b show a combination of an embodiment similar to the one shown in FIG. 2 with additional mounting means as shown in FIGS. 5a and 5b.
Figure 8B:
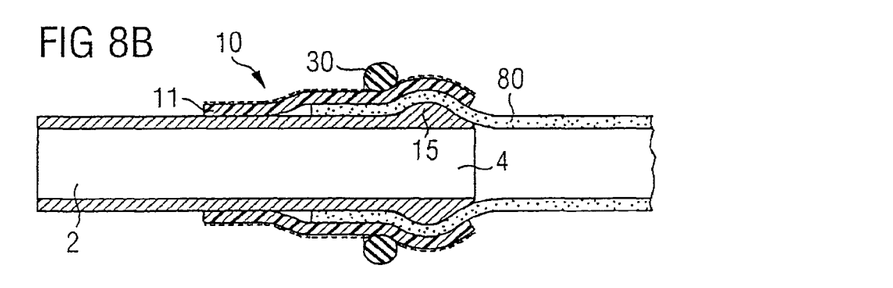

Any of the described flexible sleeve connections can be combined with the bulge locking ring locking mechanism. Of these variants, only one shall exemplary be described in the following in relation to FIGS. 8a and 8b. The embodiment shown in FIGS. 8a and 8b substantially correspond to the embodiment of FIGS. 5a and 5b, where the flexible sleeve 10 is rolled upon itself and then unrolled to cover the tubular tissue 80 which, in this case, is pulled over the second end 4 of the conduit 2 sufficiently far so as to extend also over the bulge 15. After the flexible sleeve 10 has been unrolled over the tubular tissue 80, the blocking ring 30 is pushed over the flexible sleeve against the bulge 15. After a while, the threads 20 sutured to the tubular tissue 80 and the wall 5 of the conduit 2 (FIG. 8a) will have been absorbed by the patient's body and, about during the same time, living tissue will have formed in and connect the tubular tissue 80 to the ingrowth layer 11 of the flexible sleeve 10. Therefore, as the tubular tissue 80 tends to be pulled off of the second end 4 of the conduit 2, the blocking ring 30 will also be moved, press the tubular tissue 80 and the flexible sleeve 10 against the bulge 15 and thereby prohibit any further slippage of the tubular tissue 80 over the bulge 15. The friction coefficient between the blocking ring 30 and the outer surface of the flexible sleeve should be higher than the friction coefficient which the conduit's outer surface 6 has in relation to the tubular tissue 80.

Note that the flexible sleeve 10 in its unrolled state as shown in FIG. 6b must not necessarily extend over the bulge 15 but can end a distance away from the bulge. In that situation, the blocking ring 30 would not clamp the sleeve 10 against the bulge 15 but only the living tissue 80.

The invention claimed is:

1. An implantable tissue connector adapted so as to be connectable to a tubular part of living tissue within a patient's body, comprising:
   a conduit having at least a first end and a second end and further having an outer surface with at least one bulge extending outwardly from the conduit's outer surface in a circumferential direction of the conduit about at least a part of the conduit's circumference,
   at least one blocking ring arranged on the conduit on a first side of the bulge and loosely fitting over the outer surface of the conduit with a clearance between the outer surface of the conduit and the blocking ring for mounting tubular living tissue within the clearance, said blocking ring having an inner cross sectional diameter which is smaller than or substantially identical to an outer cross sectional diameter of the at least one bulge so as to prevent the blocking ring from slipping over the bulge when living tissue axially extending over the bulge from a second side of the bulge opposite the first side is mounted within the clearance, and
   at least one flexible sleeve arranged on the conduit on the first side of the bulge and adapted to axially extend and closely fit around at least part of said outer surface of the conduit, wherein said flexible sleeve is adapted to extend over the bulge,
   wherein the implantable tissue connector is adapted for the living tissue to be pulled over the conduit's outer surface from the second side of the bulge over and beyond the bulge and said flexible sleeve arranged on the conduit on the first side of the bulge is adapted to extend over the bulge including the living tissue pulled over and beyond the bulge so as to cover the living tissue, wherein the blocking ring is adapted to be advanced from the first side of the bulge over the sleeve covering the living tissue pulled beyond the bulge, such that the living tissue is located intermediate the conduit's outer surface and the sleeve which is in contact with the bulge.

2. The tissue connector of claim 1, wherein the blocking ring is adapted to be pushed over the flexible sleeve against the bulge.

3. The tissue connector of claim 2, wherein the at least one flexible sleeve is located proximately to said first end of the conduit.

4. The tissue connector of claim 3, wherein the conduit has at least two of said flexible sleeves, and the at least two flexible sleeves are each located proximately to one of said at least first and second ends of the conduit.

5. The tissue connector of claim 2, wherein said second end of the conduit is adapted for connecting the tissue connector to at least one of the following items: an implantable reservoir, an implantable pump, an implantable motor, an implantable medical device, a biological transplant.

6. The tissue connector of claim 2, wherein between the first and second ends of the conduit or connected to the second end of the conduit, there is provided at least one of the following items: a reservoir, a pump, a motor, a medical device.

7. The tissue connector of claim 6, wherein the reservoir is artificial or a biological transplant or made from tissue material of a patient into whom the reservoir is to be implanted.

8. The tissue connector of claim 1, wherein the blocking ring is made from a material that has a friction coefficient in relation to living human mucosa tissue that is higher than a friction coefficient which the conduit's outer surface has in relation to living human serosa tissue.

9. The tissue connector of claim 1, wherein the at least one bulge is located proximately to said first end of the conduit.

10. The tissue connector of claim 1, wherein said at least one bulge comprises at least two bulges, and wherein the conduit has at least two of said bulges with the at least one blocking ring being located intermediate said at least two bulges.

11. The tissue connector of claim 10, wherein the at least one blocking ring located intermediate said at least two bulges comprises two blocking rings, each of said two blocking rings being located proximate one of said at least first and second ends of the conduit.

12. The tissue connector of claim 11, wherein the at least two bulges are each located proximate one of said at least first and second ends of the conduit.

13. The tissue connector of claim 1, wherein—depending upon the intended use—the clearance is in the range of one of the following ranges: 0.1 to 0.4 mm, 0.4 to 0.8 mm, 0.8 to 1.3 mm, 1.3 to 2 mm, 2 to 3 mm, 3 to 4 mm, 4 to 5 mm, over 5 mm.

14. The tissue connector of claim 1, wherein the flexible sleeve is made from a biocompatible material, which preferably comprises at least one polymer selected from the following group of polymers comprising: polytetrafluoroethylene, silicone, polyurethane, expanded polytetrafluoroethylene (ePTFE).

15. The tissue connector of claim 1, wherein the conduit is less flexible than the flexible sleeve at least in a radial direction so as to provide support to the flexible sleeve against radial forces.

* * * * *